United States Patent [19]

Beiler et al.

[11] 4,000,281
[45] Dec. 28, 1976

[54] PYRAZOLE DERIVATIVES

[75] Inventors: Jay Morton Beiler, Philadelphia, Pa.; Fernand Binon, Strombeek-Bever, Belgium

[73] Assignee: Richardson-Merrell Inc., Wilton, Conn.

[22] Filed: Dec. 6, 1971

[21] Appl. No.: 205,320

Related U.S. Application Data

[62] Division of Ser. No. 860,789, Sept. 24, 1969, Pat. No. 3,678,063.

[52] U.S. Cl. ............................................. 424/263
[51] Int. Cl.$^2$ ..................................... A61K 31/44
[58] Field of Search ................................. 424/263

[56] References Cited

FOREIGN PATENTS OR APPLICATIONS 1,025,697    4/1966    United Kingdom .............. 424/263

OTHER PUBLICATIONS

Antibiotic News, Vol. 5, No. 9, Oct. 1968, pp. 1 and 3.
Merck Mawuaz, 11th edition, pp. 1268–1269 (1966).
Frobishev–Fundamentals of Microbiology, Saunders Publishers, 2nd edition, pp. 71, 79 and 80 (1962).
Frobishev–Fundamentals of Microbiology, Sanders Publishers, 8th edition, pp. 234 & 235 (1969).
Cecil et al., A Textbook of Medicine, 9th ed., W. B. Saunders Co., Phila., Pa., 1958, p. 1.

Primary Examiner—Jerome D. Goldberg
Attorney, Agent, or Firm—George W. Rauchfuss, Jr.; Eugene O. Retter

[57] ABSTRACT

Pyrazole derivatives of the general formula:

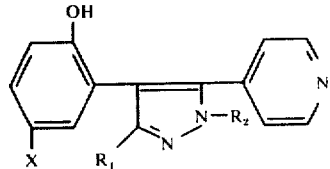

wherein $R_1$ and $R_2$ are each hydrogen, methyl, ethyl, n-propyl, isopropyl, or n-butyl and X is hydrogen, hydroxy, methyl, methoxy, chlorine, or bromine, and their acid addition salts have antiviral activity against both RNA and DNA viruses such as myxoviruses, adenoviruses, rhinoviruses, and various viruses of the Herpes group. The compounds are active when administered orally or topically. They may be prepared by heating hydrazine hydrate or an alkyl hydrazine with a 3-benzofuryl ketone.

10 Claims, No Drawings

PYRAZOLE DERIVATIVES

This application is a division of application Ser. No. 860,789 filed Sept. 24, 1969 which issued as U.S. Pat. No. 3,678,063 issued July 18, 1972.

This invention relates to pyrazole derivatives having a polyvalent antriviral action, to pharmaceutical compositions containing said derivatives and to the therapeutic use thereof. The invention also relates to a process for preparing the pyrazole derivatives.

It has been found that there is a class of pyrazole derivatives the members of which possess the unusual and unexpected property of exerting a polyvalent antiviral action, in that they have been found to be effective against both RNA and DNA viruses and especially against myxovirus, adenovirus, rhinoviruses and various viruses of the Herpes group. It has also been observed that compounds in this class tend to exert an influence upon cellular proliferation and metabolism.

This class of pyrazole derivatives can be represented by the general formula:

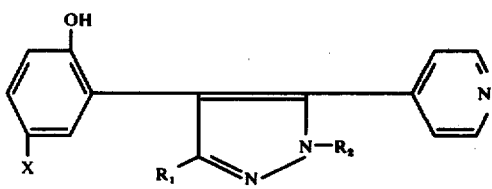

wherein $R_1$ and $R_2$, which may be the same or different, represent hydrogen, methyl, ethyl, n-propyl, isopropyl or n-butyl; and X represents hydrogen, hydroxy, methyl, methoxy, chlorine or bromine.

Examples of compounds falling within the definition of formula I are 3-(4-pyridyl)-4-(2-hydroxyphenyl)-5-ethylpyrazole, its 5-methyl, 5-n-propyl, 5-isopropyl and 5-n-butyl homologues, 3-(4-pyridyl)-4-(2-hydroxy-5-methoxyphenyl)-5-methylpyrazole, 2-methyl-3-(4-pyridyl)-4-(2-hydroxyphenyl)-5-ethylpyrazole and its 2-isopropyl and 2-n-butyl homologues.

The pyrazole derivatives represented by formula I form acid addition salts with either inorganic or organic acids, for example, hydrochloric acid and oxalic acid, and hence the pharmaceutically acceptable acid addition salts of the compounds of formula I, which, as would be expected, also have the aforementioned polyvalent antiviral action, may be employed if desired instead of the free base.

Thus, in accordance with one aspect of the present invention there is provided a pharmaceutical composition for prophylactic or curative use against RNA and DNA viruses, the composition being in a form suitable for topical or intranasal administration and comprising as an essential active ingredient a pyrazole derivative represented by formula I, or a pharmaceutically acceptable acid addition salt thereof, and a pharmaceutical carrier therefor.

The pharmaceutical composition can be in the form of, for example, an ointment for topical application or a solution or suspension for intranasal administration and hence the pharmaceutical carrier may be, for example, an ointment base, distilled water, or an emulsifying medium containing one or more emulsifying agents. The composition may contain, for example, from 1 to 20%, preferably 1 to 10%, by weight, of the active ingredient, the actual amount varying according to the mode of administration employed and to whether the composition is to be employed for curative or prophylactic use.

The pyrazole derivatives represented by formula I can be prepared in accordance with the invention by the use of a known procedure, such as, for example, by heating with hydrazine hydrate or with an appropriate alkyl hydrazine, a 3-benzofuryl ketone represented by the general formula:

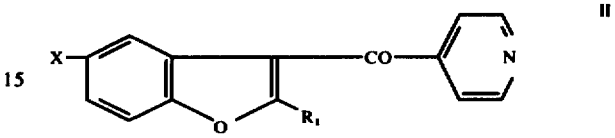

wherein $R_1$ and X have the same meanings as in formula I, in accordance with the method described in Bull. Soc. Chim. Belg. 73, 459—482, 1964, and isolating the corresponding pyrazole derivative which forms. The reactants are preferably heated in an inert organic medium, for example, methanol, ethanol or isopropanol.

The starting products represented by formula II wherein $R_1$ is other than hydrogen can be prepared, for example, by reacting the hydrochloride of isonicotinoyl chloride with an appropriate 2-alkyl-benzofuran optionally substituted in the 5-position, by the method described in Chimie Therapeutique 2, 119, 1967, whilst the starting products in which $R_1$ is hydrogen can be prepared in a similar manner using an appropriate benzofuran, by the method described in Bull. Soc. Chim. France 1952, 1056–1060.

The acid addition salts of the compounds of formula I can be prepared by treatment of the free base with an appropriate acid usually in the presence of an organic medium, for example, an alcohol.

As mentioned above, the pyrazole derivatives represented by formula I have been found to possess a polyvalent antiviral action. Biological tests have been carried out with a view to determining the polyvalent antriviral activity of the compounds of formula I with respect to certain viruses of the RNA and DNA groups. The viruses were given in lethal dilutions made up of multiples of the concentration required to kill 50% of untreated animals ($LD_{50}$).

As regards the RNA class of virus, three types of test (Tests Nos. 1, 2 and 3) were performed on mice using various Influenza viruses.

Test No. 1 (Mouse-Survival Test)

The mice were first divided into two groups. The animals of one group were given, either by intraperitoneal (IP) or by oral (PO) route, the compound to be tested, suspended in 0.25 percent of carboxymethylcellulose. One hour later they were infected with a dilution of the virus by aerosol. Further doses of the compound to be tested, of the same concentration as the first, were then given by the same route, 3, 24, 48 and 72 hours after infection. The animals of the other group, which constituted the control group, were infected in the same manner as the treated animals but did not receive any compound of the invention.

In the course of the test, which lasted fifteen days, the following data were registered:

a. The Mean Day of Death (MDD) expressed in days for both the treated and control groups.
b. The ratio of the MDD of treated animals to the MDD of control animals giving the Survival Index (SI). The SI was considered significant if it exceeded 1.24.
c. The percentage of treated aniamls surviving at the end of the test.

The compounds of the invention employed in the first series of trials were 3-(4-pyridyl)-4-(2-hydroxyphenyl)-5-ethylpyrazole (Compound A), its 5-methyl (Compound B), 5-n-propyl (Compound C), 5-isopropyl (Compound D) and 5-n-butyl (Compound E) homologues, 3-(4-pyridyl)-4-(2-hydroxy-5-methoxyphenyl)-5-methylpyrazole (Compound F), 2-methyl-3-(4-pyridyl)-4-(2-hydroxyphenyl)-5-ethyl-pyrazole (Compound G) and its 2-isopropyl (Compound H) and 2-n-butyl (Compound I) homologues. All these compounds can of course exist in the form of a pharmaceutically acceptable acid addition salt thereof.

The following results were registered:

| Com- pound | Route | Dose mg/kg | Survival Percent | S.I. | Virus Dose Multiples of $LD_{50}$ |
|---|---|---|---|---|---|
| A | IP | 500 | 37.5 | 1.71 | 25 |
|   | IP | 50 | 0 | 1.37 | 25 |
|   | PO | 500 | 33.3 | 1.71 | 56 |
| B | IP | 500 | 0 | 1.29 | 56 |
| C | IP | 500 | 50 | 1.84 | 32 |
| D | IP | 500 | 100 | 2.69 | 13 |
|   | IP | 50 | 0 | 1.31 | 13 |
|   | IP | 5 | 0 | 1.36 | 13 |
|   | PO | 500 | 60 | 2.14 | 16 |
|   | PO | 50 | 40 | 1.67 | 16 |
| E | IP | 500 | 10 | 1.62 | 56 |
|   | IP | 50 | 10 | 1.30 | 56 |
| F | IP | 500 | 0 | 1.29 | 28 |
| G | IP | 500 | 60 | 2.17 | 25 |
|   | IP | 50 | 0 | 1.30 | 25 |
| H | IP | 500 | 30 | 1.91 | 21 |
|   | IP | 50 | 0 | 1.35 | 21 |
| I | IP | 500 | 14 | 1.91 | 21 |
|   | IP | 50 | 0 | 1.48 | 21 |
|   | IP | 5 | 0 | 1.32 | 21 |

In another series of trials with compounds A and D but involving other Influenza viruses, the following results were obtained.

| Com- pound | Dose mg/kg | Route | Virus | Virus Dose Multiples of $LD_{50}$ | Survival Percent | S.I. |
|---|---|---|---|---|---|---|
| A | 500 | IP | Jap 305 | 32 | 60 | 2.04 |
|   | 50 | IP |   | 32 | 10 | 1.34 |
|   | 500 | PO |   | 3.2 | 66 | 1.43 |
|   | 50 | PO |   | 3.2 | 60 | 1.43 |
|   | 5 | IP |   | 20 | 20 | 1.34 |
| A | 500 | IP | Maryland B | 79 | 10 | 1.47 |
|   | 500 | PO |   | 79 | 12 | 1.52 |
| A | 500 | IP | Swine A | 14 | 50 | 1.52 |
| D | 500 | PO | Jap 305 | 15 | 100 | 2.12 |
|   | 50 | PO |   | 15 | 30 | 1.31 |
|   | 500 | IP |   | 22 | 70 | 2.16 |

Taking 1.24 as the minimum significant Survival Index figure, the above Tables show that the compounds so tested were effective in prolonging the survival time of mice exposed to lethal dilutions of various Influenza viruses.

Test No. 2(48-Hour Mouse Test)

This test was undertaken for the purpose of studying the effects of the compounds of the invention on different viruses during the early stages of the virus growth cycle in the mouse.

The mice were divided into three groups. The first two groups received a dose of the compound to be tested, one group by intraperitoneal (IP) route and the other by oral (PO) route. One hour later, all three groups were infected with a dilution of the virus by aerosol. Further doses of the compound to be tested, of the same concentration as the first, were then given to the first two groups by the same route 3 hours and 24 hours after infection. The third, untreated, group constituted the control group. Forty-eight hours after infection the treated groups were sacrificed simultaneously with the control group. The lungs from each group were removed, pooled separately by group, and ground in a hydrolysate of casein to form three 10% homogenates. Two series of dilutions, in which each dilution was one tenth of the concentration of the preceding dilution, were prepared from the homogenates obtained from the treated animals. These dilutions were subsequently injected (0.2 ml/egg) into 11-day-old embryonated chicken eggs for titration of the egg infectivity of the virus contained in the mouse lung material. Six eggs were infected with each dilution of virus. After incubation for 48 hours at 37° C. the eggs were chilled and the allantoic fluid from the eggs collected. A haemagglutination pattern was obtained by adding 0.5 ml of a fresh 0.5% suspension of chick erythrocytes to an equal volume of allantoic fluid from each egg. The titre at which the 50% endpoint of egg infectivity ($EID_{50}$) occurred was calculated from the results of the haemagglutination test. These results were compared with that obtained by the same process using lung material from the control animals. A one-log reduction in $EID_{50}$ as compared with the control figure was considered significant.

The compound of the invention used in this test was 3-(4-pyridyl)-4-(2-hydroxyphenyl)-5-ethylpyrazole. The results obtained with this compound against the different viruses employed are given hereunder:

| VIRUS | COMPOUND Dose mg/kg | Route | Log Reductions as compared with controls | Virus dose Multiples of $LD_{50}$ |
|---|---|---|---|---|
| Influenza PR8 | 500 | IP | −1.87 | Not ascertained |
|   | 50 | IP | −1.69 | " |
|   | 5 | IP | −1.41 | " |
|   | 500 | PO | −1.07 | " |
|   | 50 | PO | −1.21 | " |
| Jap 305 | 50 | IP in HCl | −1.53 | 20 |
|   | 500 | PO | −2.5 | 3.2 |
|   | 50 | PO | −2.7 | 3.2 |
|   | 5 | PO | −2.0 | 3.2 |
| Swine A | 500 | IP | −1.8 | 14 |
|   | 50 | IP | −1.0 | 14 |
|   | 50 | PO | −1.4 | 14 |
|   | 5 | PO | −1.1 | 14 |

Test No. 3 (Intranasal)

Tests were performed to determine the efficacy against an Influenza virus of 3-(4-pyridyl)-4-(2-hydroxyphenyl)-5-ethypyrazole (Compound A) administered intranasally to mice. The test compound was given in various concentrations and at various times before infection by aerosol with an appropriate dilution of the virus. The results obtained with a 10% suspension of the test compound as compared with those obtained with the diluent used for the suspension in mice infected with 25 multiples of the $LD_{50}$ dose of the virus, are given below:

| AGENT | Time of Administration before Infection | SURVIVAL | | | Virus Dose Multiples of $LD_{50}$ |
| --- | --- | --- | --- | --- | --- |
| | | Percent | MDD | S.I. | |
| Compound A | 6 hr. | 50 | 11.80 | 1.90 | 25 |
| | 4 hr. | 60 | 11.70 | 1.88 | 25 |
| | 2 hr. | 70 | 12.80 | 2.07 | 25 |
| | 30 min. | 40 | 11.80 | 1.90 | 25 |
| Diluent | 6 hr. | 0 | 5.97 | 0.964 | 25 |
| | 30 min. | 0 | 5.70 | 0.920 | 25 |
| Virus alone | | 0 | 6.20 | — | 25 |

The results showed that the test compound exerted a definite protective effect at all times of administration. Between 40% and 70% of the animals survived the test period as compared to 100% mortality in the untreated controls. The survival period of the treated animals that did die was increased to approximately twice that of the controls. Persistance of the effect was marked since no significant differences were seen between the results obtained with the various times of administration of the test compound.

A similar intranasal test conducted with various concentrations of 3-(4-pyridyl)-4-(2-hydroxyphenyl)-5-isopropyl-pyrazole (Compound D) in suspension administered 30 minutes before infection by aerosol with Influenza virus Jap 305 gave the following results:

| COMPOUND Concentration | Number of Doses | SURVIVAL | | | Virus Dose Multiples of $LD_{50}$ |
| --- | --- | --- | --- | --- | --- |
| | | Percent | MDD | S.I. | |
| 10% | 1 | 60 | 13.00 | 1.84 | 15 |
| 5% | 1 | 30 | 9.76 | 1.38 | 15 |
| 2.5% | 1 | 40 | 10.50 | 1.49 | 15 |

Other tests were carried out to determine the inhibitory effect of 3-(4-pyridyl)-4-(2-hydroxyphenyl)-5-ethylpyrazole on various types of rhinovirus.

In each test two cultures of human embryonic lung were prepared of which one was treated with the above compound while the other served as control. The cultures were then infected with a strain of rhinovirus. The compound was used in concentrations of 50 and 75 μgm/ml and was considered to be active if the cytopathogenic effect of the rhinovirus was reduced by at least 75% as compared to the control culture. This cytopathogenic effect was determined by counting the number of plaques formed by destroyed cells.

Seven human types of rhinovirus were employed and the following results registered:

| RHINOVIRUS | | ACTIVITY |
| --- | --- | --- |
| Type | Strain | (+ = active) |
| 3 | prototype | + |
| 5 | prototype | + |
| 6 | SF1349 | + |
| 7 | SF1470 | + |
| 8 | prototype | + |
| 9 | prototype | + |

-continued

| RHINOVIRUS | | ACTIVITY |
| --- | --- | --- |
| 14 | prototype | + |

A further series of tests was performed in which the inhibitory concentrations of 3-(4-pyridyl)-4-(2-hydroxyphenyl)-5-ethylpyrazole against various human types of rhinovirus were determined by the gradient plate plaque-reduction technique. Cultures of HeLa cancer cells were used of which two were prepared for each test. One culture was treated with the above compound which was applied in gradient while the other culture served as control. Both cultures were then infected with a human type of rhinovirus. The inhibitory concentration was determined by measuring the zone of inhibition on the cellsheet. Six types of rhinovirus were employed and the following results registered.

| RHINOVIRUS | | MINIMUM INHIBITORY Concentration (μgm/ml) | ACTIVITY + = active − = inactive |
| --- | --- | --- | --- |
| Type | Strain | | |
| 14 | 1059 | 30 | — |
| 27 | Cor. 28 | 15–16 | + |
| 39 | 209 | ca.16 | + |
| 44 | F01 3744 | 30 | — |
| 50 | $A_2$ No.58 | ca.25 | + |
| 55 | Wis 315E | 20 | + |

With regard to viruses of the DNA group, tissue culture tests were performed to determine the activity of 3-(4-pyridyl)-4-(2-hydroxyphenyl)-5-ethylpyrazole against Herpes Simplex. The test material employed was rabbit kidney tissue. In a test involving pretreatment of virus with the compound, equal volumes of the compound and of the virus were incubated together in test tubes for one hour at room temperature. This mixture was then inoculated into a bottle containing the rabbit kidneytissue. The bottle was incubated at 36° C. for two hours after which the fluids were discarded and 5 ml. of overlay added. After four days, the overlay was removed and crystal violet stain added for five minutes. The plaques appeared as clear areas in a blue background. A plaque-reduction of 50% was considered as significant. The same procedure was followed in a second test with the exception that the rabbit kidney tissue was first infected and the compound incorporated into the overlay. It was found that a dose of 250 μg caused 60% plaque-reduction in the first test and 100% plaque-reduction in the second test.

Another test was caried out with this same compound in order to evaluate its action against Herpes-induced keratitis in the rabbit eye. The compound was used locally in concentrations of 2, 1 and 0.5% and it was found that, at all three dosage levels, the compound inhibited the formation of geographic keratitic lesions as compared to the infected control animals.

Preliminary biological tests have indicated that compounds falling within the definition of formula I exert an effect against adenoviruses, parainfluenza virus and rhinoviruses.

The following examples illustrate the preparation and formulation into pharmaceutical compositions of compounds in accordance with the invention.

EXAMPLE 1

Preparation of 3-(4-pyridyl)-4-(2-hydroxyphenyl)-5-ethylpyrazole and its hydrochloride.

In a 20-liter three-necked reactor fitted with an ascending condenser, a dropping-funnel and a mechanical stirrer, were placed 1455 g. (5.80 mol) of 2-ethyl-3-isonicotinoylbenzofuran and 10 liters of isopropanol. The resulting solution was stirred and 447 ml. of 98% hydrazine hydrate dissolved in 1455 ml. of isopropanol were slowly added. During the operation, the temperature of the reaction medium gradually increased so as to reach 60° C. when all the hydrazine hydrate solution had been added. The solution was refluxed for 15 minutes and then allowed to cool to room temperature. The precipitate which formed was centrifuged out and washed with 500 ml. of isopropanol.

In this way a first fraction of 1175 g. of 3-(4-pyridyl)-4-(2-hydroxyphenyl)-5-ethylpyrazole was obtained.

The isopropanol mother liquor was evaporated under vacuum until new crystals appeared which were then centrifuged out and taken up in 2 liters of isopropanol. The suspension was centrifuged and a second fraction of 250 g. of the desired product obtained.

The total amount of 3-(4-pyridyl)-4-(2-hydroxyphenyl)-5-ethylpyrazole thus prepared was 1425 g. representing a yield of 92.8%. M.P. 243°–244° C.

In the foregoing example, ethanol or methanol may be used in place of the isopropanol and the end-product may be purified by crystallization from ethanol or methanol instead of from isopropanol.

To prepare the hydrochloride, 53 g. (0.2 mol) of 3-(4-pyridyl)-4-(2-hydroxyphenyl)-5-ethylpyrazole were suspended in 300 ml. of isopropanol. To this was added 20 ml. of concentrated hydrochloric acid (37%) and 20 ml. of distilled water and the suspension heated until the pyrazole was completely dissolved. The hot solution was then passed through a filter and the filtrate allowed to cool while being slowly stirred. The hydrochloride crystals which formed were filtered out, washed over a filter with isopropanol and dried under vacuum. Yield: 51.8 g (86%). M.P.: Decomposition at ca. 260° C.

By the same procedure as that described in the foregoing example, the following compounds were prepared from the starting compound indicated:

From 2-methyl-3-isonicotinoyl-benzofuran M.P. 80° C., 3-(4-pyridyl)-4-(2-hydroxyphenyl)-5-methyl-pyrazole M.P. 260° C.

From 2-n-butyl-3-isonicotinoyl-benzofuran M.P. 52° C., 3-(4-pyridyl)-4-(2-hydroxyphenyl)-5-n-butyl-pyrazole M.P. 238° C.

From 2-n-propyl-3-isonicotinoyl-benzofuran B.P. 145°–150° Co/0.005 mm. Hg., 3-(4-pyridyl)-4-(2-hydroxyphenyl)-5-n-propyl-pyrazole M.P. 250° C.

From 2-methyl-3-isonicotinoyl-5-methoxy-benzofuran M.P. 45° C., 3-(4-pyridyl)-4-(2-hydroxy-5-methoxyphenyl)-5-methylpyrazole M.P. 232° C.

From 2-ethyl-3-isonicotinoyl-5-chlorobenzofuran M.P. 98° C., 3-(4-pyridyl)-4-(2-hydroxy-5-chlorophenyl)-5-ethylpyrazole M.P. 298° C.

From 2-ethyl-3-isonicotinoyl-5-methylbenzofuran M.P. (Hydrochloride) 170° C. (decomp), 3-(4-pyridyl)-4-(2-hydroxy-5-methylphenyl)-5-ethyl-pyrazole M.P. 276° C.

From 2-ethyl-3-isonicotinoyl-5-bromo-benzofuran M.P. 90° C., 3-(4-pyridyl)-4-(2-hydroxy-5-bromophenyl)-5-ethylpyrazole M.P. 290° C.

From 2-isopropyl-3-isonicotinoyl-benzofuran M.P. (Hydrochloride) 165° C. (decomp.), 3-(4-pyridyl)-4-(2-hydroxyphenyl)-5-isopropylpyrazole M.P. 222° C.

From 3-isonicotinoyl-benzofuran M.P. 145° C., 3-(4-pyridyl)-4-(2-hydroxyphenyl)-pyrazole M.P. 220° C.

EXAMPLE 2

Preparation of 2-methyl-3-(4-pyridyl)-4-(2-hydroxyphenyl)-5-ethylpyrazole

In a one-liter flask fitted with an ascending condenser was placed 45 g. (0.18 mol) of 2-ethyl-3-isonicotinoyl-benzofuran, 400 ml. of absolute ethanol and 27 g. of methylhydrazine. The solution was refluxed for 10 hours and then allowed to cool at room temperature. The precipitate which formed was centrifuged, washed with a small quantity of absolute ethanol and dried under vacuum. The resulting product was recrystallized from absolute ethanol. In this way, 33.9 g. of 2-methyl-3-(4-pyridyl)-4-(2-hydroxphenyl)-5-ethylpyrazole was obtained, melting at 236° C. Yield: 68%.

To prepare the hydrochloride, 50 g. (0.18 mol) of 2-methyl-3-(4-pyridyl)-4-(2-hydroxyphenyl)-5-ethyl-pyrazole was suspended in 250 ml. of isopropanol. To this was added 16.2 cc. of concentrated hydrochloric acid (37%) and the suspension heated until the pyrazole was completely dissolved. The hot solution was then passed through a filter and the filtrate allowed to cool while being slowly stirred. The hydrochloride crystals which formed were filtered out, washed over a filter with isopropanol and dried under vacuum. Yield: 45 g. (80.3%) M.P. Decomposition at ca. 230° C.

By the same procedure as that described in the foregoing example, the following compounds were prepared from the starting compounds indicated:

From 2-methyl-3-isonicotinoyl-benzofuran M.P. 80° C. and methylhydrazine, 2,5-dimethyl-3-(4-pyridyl)-4-(2-hydroxyphenyl)-pyrazole M.P. 213° C.

From 2-isopropyl-3-isonicotinoyl-benzofuran M.P. (HCl) 165° C. and methylhydrazine, 2-methyl-3-(4-pyridyl)-4-(2-hydroxphenyl)-5-isopropylpyrazole M.P. 247° C.

From 2-n-butyl-3-isonicotinoyl-benzofuran M.P. 52° C. and methylhydrazine, 2-methyl-3-(4-pyridyl)-4-(2-hydroxyphenyl)-5-n-butylpyrazole M.P. 126° C.

From 2-methyl-3-isonicotinoyl-benzofuran M.P. 80° C. and ethylhydrazine, 2-ethyl-3-(4-pyridyl)-4-(2-hydroxyphenyl)-5-methylpyrazole M.P. 158° C.

From 2-ethyl-3-isonicotinoyl-benzofuran M.P. 58° C. and ethylhydrazine, 2,5-diethyl-3-(4-pyridyl)-4-(2-hydroxyphenyl)-pyrazole M.P. 191° C.

From 2-n-butyl-3-isonicotinoyl-benzofuran M.P. 52° C. and ethylhydrazine, 2-ethyl-3-(4-pyridyl)-4-(2-hydroxyphenyl)-5-n-butylpyrazole M.P. 163° C.

From 2-ethyl-3-isonicotinoyl-benzofuran M.P. 58° C. and n-propylhydrazine, 2-n-propyl-3-(4-pyridyl)-4-(2-hydroxyphenyl)-5-ethylpyrazole M.P. 175° C.

From 2-methyl-3-isonicotinoyl-benzofuran M.P. 80° C. and isopropylhydrazine, 2-isopropyl-3-(4-pyridyl)-4-(2-hydroxyphenyl)-5-methylpyrazole M.P. 217° C.

From 2-ethyl-3-isonicotinoyl-benzofuran M.P. 58° C. and isopropylhydrazine, 2-isopropyl-3-(4-pyridyl)-4-(2-hydroxyphenyl)-5-ethylpyrazole M.P. 172° C.

From 2-isopropyl-3-isonicotinoyl-benzofuran M.P. (HCl) 165° C. and isopropylhydrazine, 2,5-diisopropyl-3-(4-pyridyl)-4-(2-hydroxyphenyl)-pyrazole M.P. 177° C.

From 2-n-butyl-3-isonicotinoyl-benzofuran M.P. 52° C. and isopropylhydrazine, 2-isopropyl-3-(4-pyridyl)-4-(2-hydroxyphenyl)-5-n-butylpyrazole M.P. 164° C.

From 2-ethyl-3-isonicotinoyl-benzofuran M.P. 58° C. and n-butylhydrazine, 2-n-butyl-3-(4-pyridyl)-4-(2-hydroxyphenyl)-5-ethylpyrazole M.P. 170° C.

From 2-isopropyl-3-isonicotinoyl-benzofuran M.P. (HCl) 165° C. and n-butylhydrazine, 2-n-butyl-3-(4-pyridyl)-4-(2-hydroxyphenyl)-5-isopropylpyrazole M.P. 212° C.

From 2-n-butyl-3-isonicotinoyl-benzofuran M.P. 52° C. and n-butylhydrazine, 2,5-di-n-butyl-3-(4-pyridyl)-4-(2-hydroxyphenyl)-pyrazole M.P. 121° C.

EXAMPLE 3

An ointment suitable for topical application was prepared in accordance with the known pharmaceutical techniques from the following ingredients:

| | |
|---|---|
| 3-(4-pyridyl)-4-(2-hydroxyphenyl)-5-ethylpyrazole | 2 g. |
| Ointment base | 98 g. |
| | 100 g. |

EXAMPLE 4

Suspensions for nasal installation containing 5% and 10% w/v respectively of active compound were prepared in accordance with known pharmaceutical techniques from the following ingredients:

| | 5% | 10% |
|---|---|---|
| 3-(4-pyridyl)-4-(2-hydroxyphenyl)-5-ethyl-pyrazole | 5 g. | 10 g. |
| Propylene glycol | 5 g. | 5 g. |
| Emulsion Antifoam AF | 0.1 g. | 0.1 g. |
| Polyoxyethylene (20) sorbitan monooleate | 0.1 g. | 0.1 g. |
| Methyl p-hydroxybenzoate | 0.1 g. | 0.1 g. |
| Propyl p-hydroxybenzoate | 0.015 g. | 0.015 g. |
| Methylcellulose (4000 cP.) | 0.65 g. | 0.5 g. |
| Water (distilled)    q.s. to give | 100 ml. | 100 ml. |

The defoamer "Emulsion Antifoam AF" is a commercially available product marketed by Dow Corning and is stated to be a 30% silicone (simethicone) defoamer in a nonionic solution.

EXAMPLE 5

A 1% solution for intranasal administration was prepared in accordance with known pharmaceutical techniques from the following ingredients:

| | |
|---|---|
| 3-(4-pyridyl)-4-(2-hydroxyphenyl)-5-ethylpyrazole hydrochloride | 1 g. |
| Water (distilled)    q.s. to give | 100 ml. |

We claim:

1. A method for the inhibition of viral infections in an animal host, wherein the virus is of the myxovirus, adenovirus, rhinovirus or Herpes virus types, which comprises administering to said host an antivirally effective amount of a pyrazole derivative of the formula:

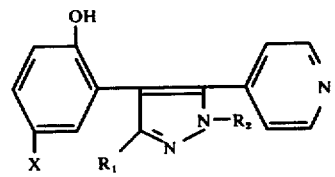

wherein $R_1$ and $R_2$ are each selected from hydrogen, methyl, ethyl, n-propyl, isopropyl and n-butyl and X is selected from hydrogen, hydroxy, methyl, methoxy, chlorine and bromine, and the pharmaceutically acceptable acid addition salts thereof.

2. A method in accordance with claim 1 in which $R_1$ is ethyl and $R_2$ and X are hydrogen.

3. A method in accordance with claim 2 in which $R_1$ is methyl and $R_2$ and X is hydrogen.

4. A method in accordance with claim 1 in which $R_1$ is n-propyl and $R_2$ and X are hydrogen.

5. A method in accordance with claim 1 in which $R_1$ is isopropyl and $R_2$ and X are hydrogen.

6. A method in accordance with claim 1 in which $R_1$ is n-butyl and $R_2$ and X are hydrogen.

7. A method in accordance with claim 1 in which $R_1$ is methyl, $R_2$ is hydrogen, and X is methoxy.

8. A method in accordance with claim 1 in which $R_1$ is ethyl, $R_2$ is methyl and X is hydrogen.

9. A method in accordance with claim 1 in which $R_1$ is ethyl, $R_2$ is isopropyl and X is hydrogen.

10. A method in accordance with claim 1 in which $R_1$ is ethyl, $R_2$ is n-butyl and X is hydrogen.

* * * * *

UNITED STATES PATENT AND TRADEMARK OFFICE
CERTIFICATE OF CORRECTION

PATENT NO. : 4,000,281
DATED : December 28, 1976
INVENTOR(S) : Fernand Binon and Jay Morton Beiler It is certified that error appears in the above-identified patent and that said Letters Patent are hereby corrected as shown below:

Column 1, line 8, "antriviral" should read "antiviral".
Column 3, line 7, "aniamls" should read "animals". Column 6, line 65, "caried" should read "carried". Column 7, line 67, "145°-150° Co/0.005" should read "145°-150°C/0.005. Claim 3, line 1, column 10, "in accordance with claim 2" should read "in accordance with claim 1".

Signed and Sealed this

Ninth Day of May 1978

[SEAL]

Attest:

RUTH C. MASON
Attesting Officer

LUTRELLE F. PARKER
Acting Commissioner of Patents and Trademarks